United States Patent [19]

Korber et al.

[11] Patent Number: 4,950,162
[45] Date of Patent: Aug. 21, 1990

[54] FRAMEWORK FOR PRODUCING TOOTH-REPLACING BRIDGES

[76] Inventors: Karlheinz Korber, Hohrott 15, 2305 Heickendorf; Klaus Ludwig, Auf der Tenne 14, 2300 Kronshagen, both of Fed. Rep. of Germany

[21] Appl. No.: 224,604

[22] Filed: Jul. 27, 1988

Related U.S. Application Data

[63] Continuation-in-part of Ser. No. 765,438, Aug. 14, 1985, abandoned.

[30] Foreign Application Priority Data

Aug. 18, 1984 [DE] Fed. Rep. of Germany ....... 3430448
Jul. 26, 1985 [EP] European Pat. Off. ........ 85-109398.9

[51] Int. Cl.$^5$ ............................................ A61C 13/225
[52] U.S. Cl. .................................... 433/180; 433/178
[58] Field of Search ............... 433/180, 181, 182, 183, 433/178

[56] References Cited

U.S. PATENT DOCUMENTS

| | | | |
|---|---|---|---|
| 446,769 | 2/1891 | Clowes | 433/180 |
| 1,211,494 | 1/1917 | Shaw | 433/181 |
| 2,002,048 | 5/1935 | Thomas | 433/172 |
| 2,213,963 | 10/1940 | Myerson | 433/191 |
| 2,411,001 | 11/1946 | Rothkranz | 433/182 |
| 3,545,083 | 12/1970 | Krasne | 433/178 |
| 4,163,318 | 8/1979 | Tigani | 433/172 |
| 4,165,561 | 8/1979 | Miller et al. | 433/9 |
| 4,431,417 | 2/1984 | Weissman | 433/182 |
| 4,457,714 | 7/1984 | Klein | 433/180 |

FOREIGN PATENT DOCUMENTS

| | | | |
|---|---|---|---|
| 3335642 | 4/1984 | Fed. Rep. of Germany | 433/181 |
| 619856 | 12/1978 | Switzerland | 433/180 |

*Primary Examiner*—John J. Wilson
*Attorney, Agent, or Firm*—Charles W. Fallow; Martin P. Hoffman

[57] ABSTRACT

A prefabricated bridge framework for producing tooth-replacement bridges consists of a support bar to bridge over a gap between teeth and connecting elements for placing the support bar on bridge pillars. The bridge framework as a whole is made of a dental alloy and is capable of being adjusted automatically to the length of a gap between teeth by changing the length of the support bar. Reinforcing ribs are provided on the bottom of the support bar. This bridge framework makes superfluous the manual construction of a wax model of a framework and the subsequent casting in metal that have been required up to now. This bridge framework is always made the same qualitatively, and guarantees that the production of tooth-replacement bridges will be considerably simpler and quicker.

17 Claims, 5 Drawing Sheets

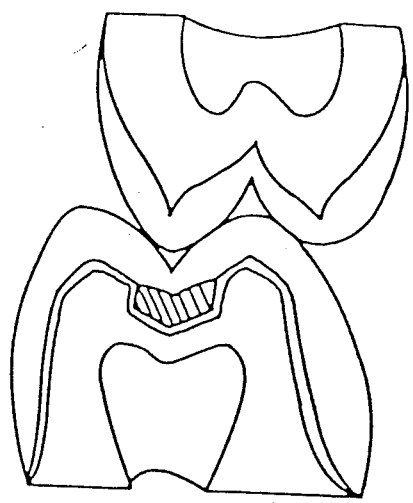
FIG. 1
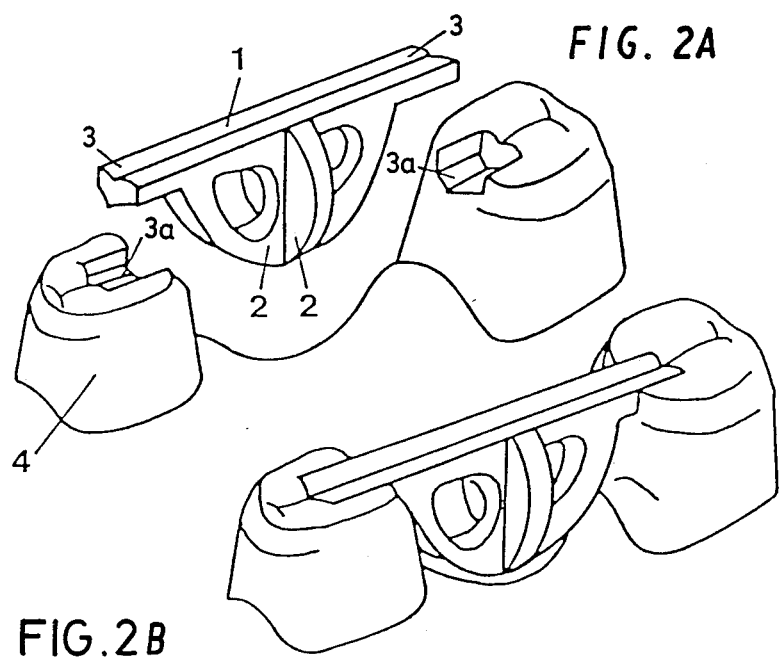
FIG. 2A
FIG. 2B

FRAMEWORK FOR PRODUCING TOOTH-REPLACING BRIDGES

CROSS-REFERENCE TO RELATED APPLICATION

This application is a continuation-in-part of application Ser. No. 765,438 filed Aug. 14, 1985, now abandoned.

BACKGROUND

This invention is concerned with a bridge framework for use in producing tooth-replacement bridges.

In all presently known procedures for producing tooth-replacement bridges made from precious metal or non-precious metal alloys, work is done in an indirect manner, since a bridge framework of wax or plastic is modeled first, and then a bridge framework of metal is cast in conformity with the model obtained in that way.

The success of this model of operation depends, to a great extent, upon the skill of the dental technician, and that is true both in making a model of the bridge framework out of wax or plastic as well as in the subsequent casting of the bridge framework made of metal. Therefore the fact that every bridge framework turns out to be different qualitatively is understandable. Furthermore, the known method of operation is labor-intensive to a high degree, and consequently it is cost-intensive at the same time.

SUMMARY OF THE INVENTION

Consequently, it is the objective of the invention to provide a bridge framework for use in producing tooth-replacement bridges that can be prefabricated industrially. The production of a tooth-replacement bridge using the bridge using the bridge framework will no longer depend upon the skill of the individual dental technician where defects in the quality of the bridges are concerned. Also, industrial production can also be considerably quicker, and therefore more desirable from the point of view of cost. In particular, it should be made possible, because the bridge frameworks can be prefabricated, to make them available in various sizes and shapes as assortments from which a bridge framework that is suitable as to the size and shape for the clinical case in question can be selected for the production of a tooth-replacement bridge.

This objective is accomplished in accordance with the invention by following a particular sequence of operational steps.

A bridge framework is actually achieved that can vary as to size and shape in such a way that an entire assortment of bridge frameworks can be produced upon which one can fall back at any time they are needed. This is realized by providing for changing the length of the support bar, which is achieved by cutting to a specific length in cases where the connecting elements are extensions of the support bar, and by employing a telescope-like construction of the support bar in cases where the connecting elements are open, or closed, ring-shaped pieces. Consequently, the bridge framework can be adjusted to fit the given length of any specific gap between teeth without any problems.

As a result of the method of manufacturing the bridge framework from a dental alloy—for example, a precious-metal alloy or even a nonprecious metal alloy—that is provided for at the time it is produced, the bridge framework is metallic and it is stable to a high degree. Its stability depends only upon the thickness of the support bar and its connecting elements that are provided for in each case. Such thickness is proportioned right from the start in such a way that sufficient allowance is made for obtaining maximum stability at optimal costs.

The reinforcement ribs provided on the bottom of the support bar, while their alignment that can possibly vary a great deal, constitute a retention and anchoring element for the facing material that is to be provided for the subsequent production of a tooth-replacement bridge—that is, for example, the tooth porcelain that is to be used, or an appropriate plastic material.

Naturally, these reinforcing ribs can be perforated or built with back tapers, in order to make as secure an anchoring as possible for the facing material.

No matter what the nature of the connecting element is, and specifically no matter whether they are extensions of the support bar or are open or closed ring-shaped pieces, these connecting elements can be settled on the bridge pillars by appropriate preparation of the pillars in such a way that they do not project out of their prepared contours. In cases where the connecting elements are extensions of the support bar, cavities are prepared in the top, or in one side of the bridging pillars; in cases where the connecting elements take the shape of ring-shaped pieces, appropriate ring-shaped receiving steps are formed on the outside of the bridge pillars.

Considerable improvement in numerous respects are achieved by the bridge frameworks of the invention. Probably the most essential improvements are the following:

A reduction of the cost: the dimensions of the bridge framework are always optimal, and they can be produced to have a weight that is minimal in relation to their cost. The time it takes to produce the bridge framework also does not depend upon the skill and ability that the dental technician may happen to have; indeed, where the cost of producing them as finished supplementary parts is concerned, calculations show them to be the best possible value in that respect.

Avoidance of deficiencies: the familiar deficiencies in the conventional production of bridge frameworks by an indirect production process involving the making of models by hand and then casting them from metal, whereby the individual errors made throughout the entire production process are cumulative, are entirely eliminated.

Resistance to breakage: by standardized, industrial production, resistance to fracture can be achieved that was not possible in the manual method of production that has been used up to now in dental technicians' laboratories.

The time factor: while the hitherto-existing method of producing tooth-replacement bridges using the bridge frameworks known until now consumes a great deal of time because of the numerous intermediate working operations that are involved. In contrast, the bridge frameworks of the invention can be installed between or on the bridge pillars or the crown anchors immediately and, in a preferred way of using them, can also be soldered there automatically, so that a tooth-replacement bridge can be produced much more quickly.

Esthetics: because of the utilization of special alloys having high stability that, practically speaking, can only be manufactured industrially, and also because of their fundamentally better potential for being shaped, the tooth-replacement bridges to be produced using the bridge framework of the invention can be given a considerably more slender shape than those made using the method of production making use of dental gold castings. Furthermore, the potential for giving a more slender shape ensures that there will be ample space for the facing material that is to be applied subsequently.

The bridge frameworks of the invention are suitable for a subsequent facing with plastic, dental-ceramic substances and porcelain. Indeed, they are also suitable for the subsequent insertion of complete plastic or porcelain teeth, and also for the attaching of external facings. The bridge frameworks of the present invention are also suitable, as the following description in detail will show, for use in connection with anchor crowns of the bridge pillars to be built up from foil caps.

In the following description, the invention will be described in greater detail with the help of examples and with the references to the drawings.

BRIEF DESCRIPTION OF THE DRAWINGS

FIG. 1 shows a vertical section through a tooth of the upper jaw and a tooth of the lower jaw, with the latter tooth having a crown, with the connecting element of a bridge framework constructed in accordance with the present invention being incorporated in the crown.

FIG. 2a shows two bridge pillars with cavities cut therein to receive the connecting elements of the bridge framework of the present invention before it is inserted into the cavities,.

FIG. 2b shows the bridge framework, with its connecting elements inserted into the cavities in the bridge pillars.

DESCRIPTION OF THE PREFERRED EMBODIMENTS

Figures 3A, 3B:
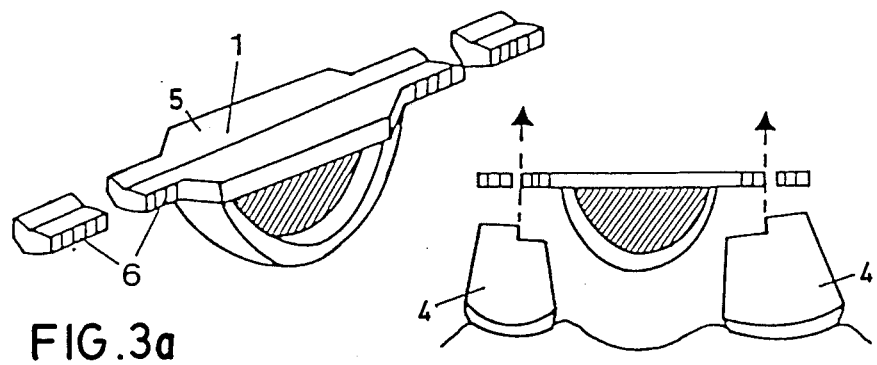
FIG. 3a shows one alternative embodiment of the bridge framework of the invention as seen in perspective, revealing the manner of changing the length of the support bar.
FIG. 3b shows the bridge framework of FIG. 3a as seen from the side in correlation with two bridge pillars to show how the length of the support bar can be adapted to the distance between the cavities that have been cut into the bridge pillars.

In a preferred embodiment shown in FIG. 2A and FIG. 2b, the carrying matrix of a bridge framework includes of a support bar 1 whose cross-section conforms to the anatomical occlusion profile (FIG. 1). The support bar 1 includes a longitudinal stiffening rib 2a which extends along its bottom surface. The rib 2a has a greatest vertical thickness in the the area of maximum bending moment, midway between the bridge pillars. The rib 2a is perforated by holes 2b, which provide retention means for facing materials. A pair of vertically extending lateral ribs 2c, 2d project from the sides of the longitudinal rib 2a, near its midpoint. The lateral ribs provide bending resistance to lateral forces, and provide additional means for retaining facing materials.

The free ends, or connecting elements, 3 of the support bar 1 are placed in cavities 3a that are cut into the bridge pillars 4, upon which the tooth-replacing bridge is to be fixed. These cavities 3a are cut into the bridge pillars 4 in accordance with the shape of the cross section of the ends 3 so that the elements fit exactly, as shown in FIG. 2b.

To facilitate adapting the prefabricated bridge framework to the distance existing between the bridge pillars 4 quickly, plural marking lines 6 are provided on the sides of the connecting elements 3 on the support bar 1, as shown in FIG. 3a. The length of the support bar 1, including the two connecting elements 3, can be adjusted by means of an appropriate tool to the existing distance between the bridge pillars 4, so that an exact fit is obtained (FIG. 3b). FIG. 3a also shows a pair of horizontal reinforcing ribs 5 extending laterally from the support bar 1.

Figure 4:
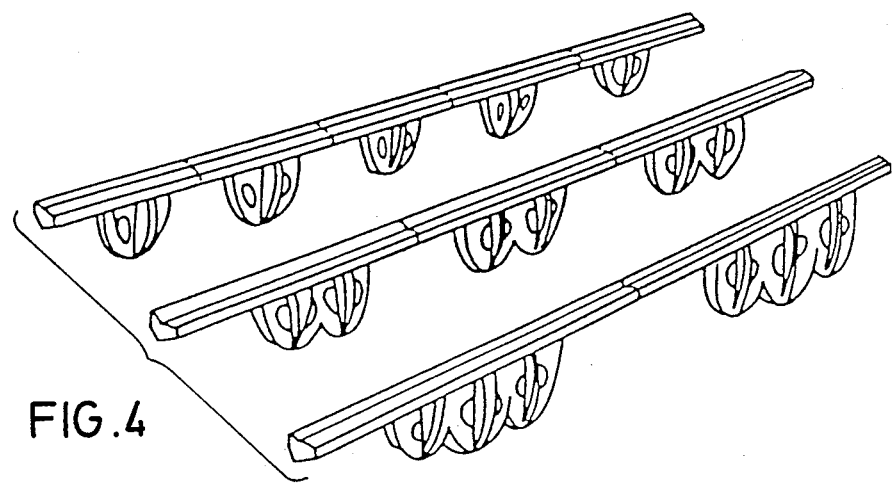
FIG. 4 shows three different bridge frameworks constructed in accordance with the present invention, arranged so that they appear one above the other. The upper bridge framework bridges over a simple gap between teeth, the middle bridge framework bridges over a gap left by two missing teeth, and the lowest bridge framework bridges over a gap left by three missing teeth.

In a further embodiment of the invention, several bridge frameworks are formed together in a continuous length of stock (FIG. 4). The separating of the required bridge frameworks from such stock can be accomplished especially economically and with a saving of material.

Figure 5:
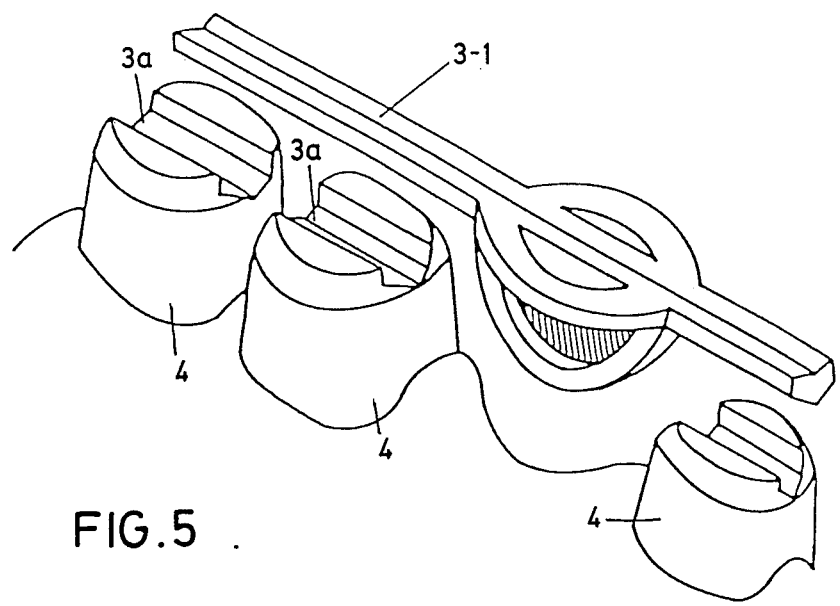
FIG. 5 shows another alternative embodiment of a bridge framework constructed in accordance with the present invention. Such bridge framework is one in which the connecting element is placed on two bridge pillars that are adjacent to each other, so that the crowns to be placed on it are interlocked with each other, so that the crowns to be placed on it are interlocked with each other above the connecting element of the bridge framework.

The possibility of interlocking several crowned teeth also exists, as shown in FIG. 5. In this embodiment, the support bar 1 is cut to the proper length, so that it can be inserted in appropriate cavities 3a in two bridge pillars that are to be interlocked with each other (FIG. 5).

Figure 6:
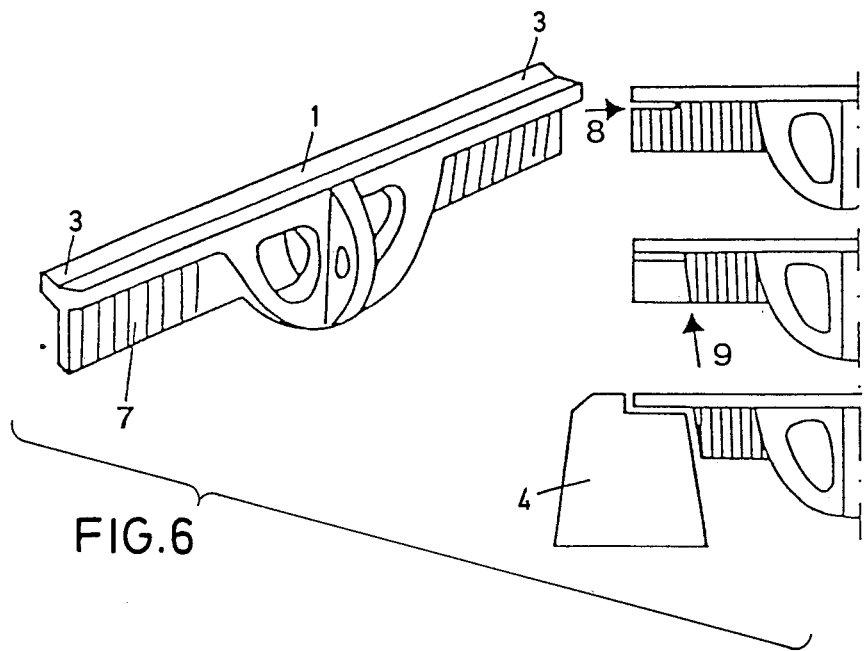
FIG. 6a shows yet another alternative embodiment of a bridge framework constructed in accordance with the invention, wherein a reinforcing rib is directed downwardly and passes through the entire length of the support bar and its connecting elements, with the reinforcing rib being attached in the central area of the bottom surfaces.
FIG. 6b shows, in sequence, how it is possible to separate a part of the reinforcing rib for the purpose of bringing about a regular adaptation to the adjacent outer surface of the bridge pillar on which the framework is to be replaced.

To guarantee sufficient stability for the support bar 1 when the distances between the bridge pillars are large, a reinforcing flange 7 extending vertically downward from the support bar is provided in the alternative embodiment of FIGS. 6a–6b. The flanges 7 extend from the bottom of the support bar 1 and connecting elements 3, to either side of the longitudinal reinforcing rib 2a. Note the perforation in the laterally extending rib 2c. The overall length of the bridge framework is adjusted to the existing distance between two bridge pillars 4 by means of two simple cuts 8 and 9, as shown in FIG. 6b. Thus the support bar is cut in such a way that it can be precisely adjusted to the size of the gap between two bridge pillars 4.

Figure 7:
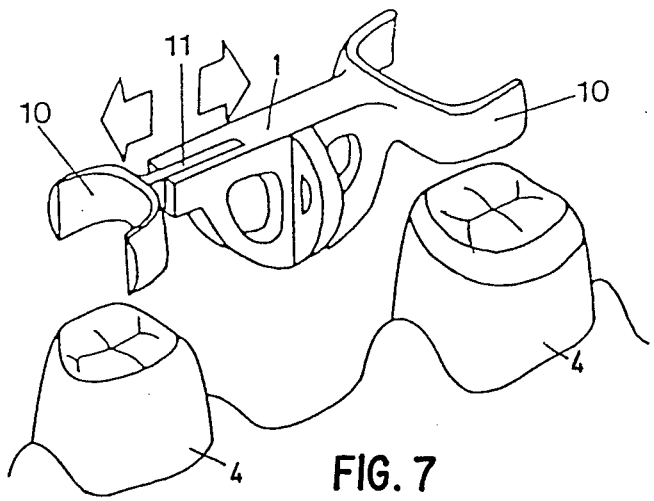
FIG. 7 shows another embodiment of the bridge framework of the invention with open ring-shaped pieces serving as connecting elements while the support bar has a telescope-like shape, with the entire device being shown positioned above two bridge pillars.
Figures 8A, 8B:
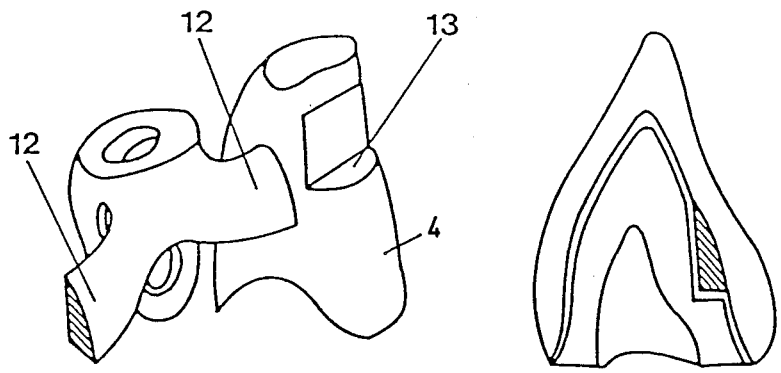
FIG. 8a depicts another alternative embodiment of the bridge framework of the invention wherein the connecting element is supported on one surface of a bridge pillar in a notch that has been appropriately prepared.
FIG. 8b depicts a cross section through an appropriately prepared bridge pillar with a connecting element in place and a crown on top of it.

The alternative embodiment of FIGS. 7–8 is applicable for special clinical conditions in which the connecting elements cannot be accommodated in cavities in the bridge pillars in the form of extensions of the support bar 1. Then the connecting elements are either open or closed ringshaped pieces 10 that envelop bridge pillars 4. To make a simple adaptation to the distance between the bridge pillars 4 possible here, too, the support bar 1 is made in two parts, like a collapsible telescoping joint 11. The telescoping joint 11 not only permits an adjustment to the distance between the bridged pillars, but it also permits any vertical adjustment of one of the ringshaped pieces 10 with respect to the other one that may be necessary. At the same time, a radial horizontal swinging of one of the pieces 10 while the other piece remains in a fixed position is also possible by the simple process of bending. Of course, a swiveling piece can also be provided on one of the two ring-shaped pieces 10 for the same purpose.

Naturally, other shapes of the connecting elements in a bridge framework constructed in accordance with the invention are also possible—for example, connecting elements 12 that can be fitted into the notches 13 in the sides of bridge pillars in conformity with the anatomical contours of the teeth (FIGS. 8 and 2b). Such embodiments are especially suitable for the area where the front teeth are located.

Figure 9:
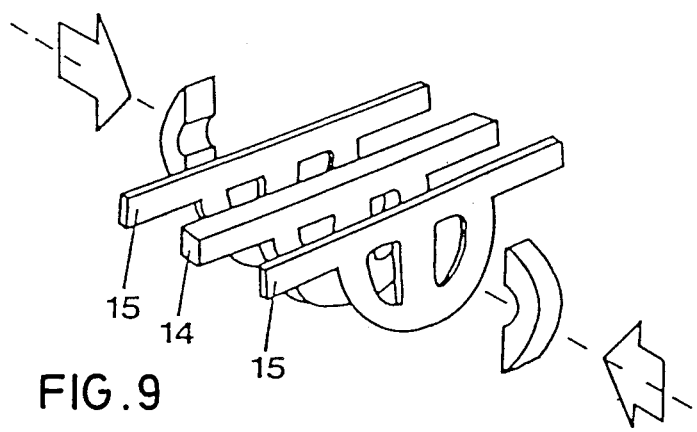
FIG. 9 shows how it is possible to build up a bridge framework constructed in accordance with the invention from several pieces located side by side at right angles to the bridge framework that are to be fastened to each other by cold welding or cold-plastic shaping.

Since the bridge frameworks of the invention are not cast in dental laboratories after models have been made—that is, they are not cast out of a single fused mass of alloy—it is possible, in a preferred embodiment, to assemble them by combining several pieces (FIG. 9) whose characteristics differ in accordance with the functions they perform. An inner core 14 of extremely hard metal or alloys with a high elasticity modulus ensures mechanical stability, while external pieces 15 made of pure gold make immediate diffusion fusion with the crown anchors possible—in a ceramic furnace, for example—and provides the esthetically important golden background for a finished tooth-replacement bridge.

Such composite frameworks are produced in a preferred manner by coldplastic shaping or cold welding from rolled material in the desired three-dimensional form. Because of the high stability of the rolled initial material, slender bridge frameworks are produced that are especially economical in regard to weight, and consequently cost less.

It is also possible to produce the bridge frameworks of the invention by means of casting, and especially from gold.

While bridge frameworks constructed in accordance with the invention and having an external piece made of pure gold permit an immediate diffusion fusion with crown anchors at temperatures above 1,063° C., the outer surfaces, and especially the coating or enveloping segments, in other embodiments are first coated with solder or a gold covering, in order also to make an automatic bonding possible and economically feasible.

In an especially preferred procedure, the bridge frameworks of the invention are used in combination with crowns that are to be placed on the bridge pillars and are manufactured with the use of so-called foil caps as a crown framework according to I. Schoher and A. Whiteman, or in accordance with the so-called Cereplatin technique.

Figure 10A:
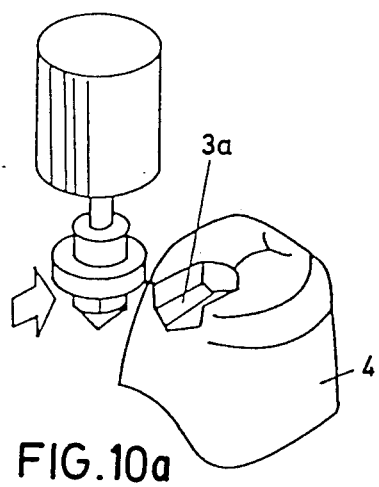
FIG. 10a shows, in perspective.
Figure 10B:
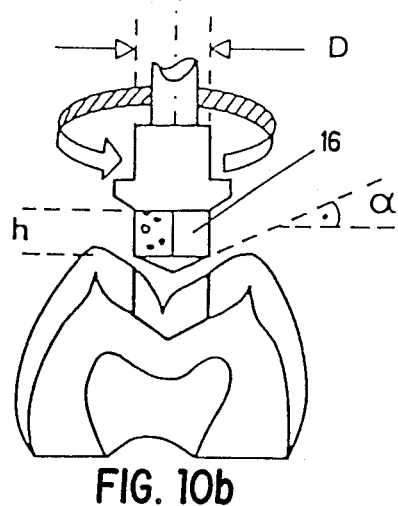
FIG. 10b shows schematically, a profile cutter for preparing the required cavities in a bridge pillar and the bridge pillar is shown in one of the drawings with a cavity already prepared.
Figure 11A:
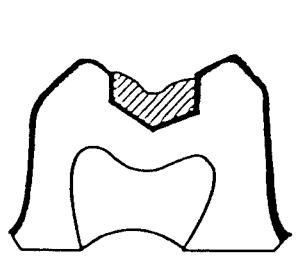
FIG. 11a shows a cross section through a bridge pillar with a cavity that has been prepared and receive a connecting element and a foil cap already put on as an anchor for the anchor crown that is to be provided on the bridge pillar, while the connecting element of a bridge framework constructed in accordance with the invention is simultaneously inserted in the cavity that is already also covered by the foil cap.
Figure 11B:
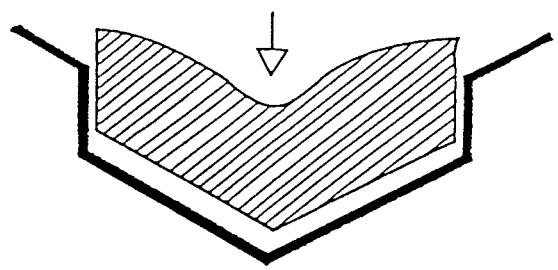
FIG. 11b shows a detail of FIG. 11a on an enlarged scale.

The connecting elements 3 are inserted in cavities 3a in the bridge pillars 4. Those cavities 3a are prepared in the masticating surfaces in accordance with the anatomical conditions by means of a standardized grinding instrument or cutter to provide a precise, three-dimensional fit. As shown in FIGS. 10a and 10b, the cutter has a cylindrical section 16 with a height h corresponding to the vertical dimension of the connecting elements 3 and an apex of prin-core with an angle α corresponding to the contour of the bottom of the connecting elements 3. If the crowns for the bridge pillars 4 are to be produced as crown frameworks using the aforementioned foil caps, that must be taken into consideration with regard to depth and the length of diagonals when preparing the cavities, as can be seen in FIGS. 11a and 11b, where the thick blade line represents the foil of the foil cap schematically.

Figure 12A:
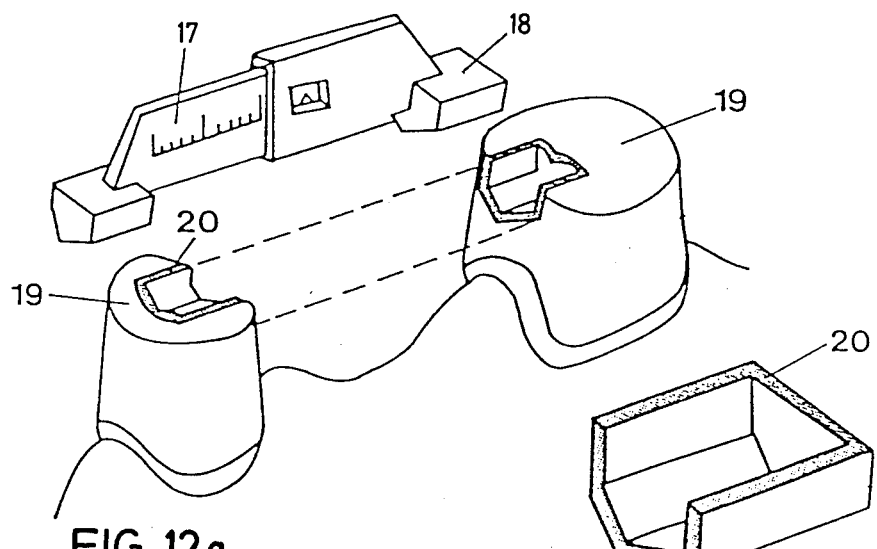
FIG. 12a shows two bridge pillars with cavities prepared, each having a plastic finished part inserted in it, and a measuring gauge.
Figure 12B:
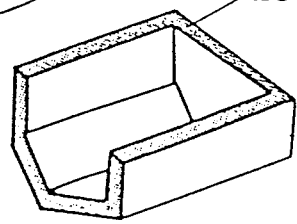
FIG. 12b shows a detail of FIG. 12a, on an enlarged scale.

The parallelism of the cavities 3a in two bridge pillars 4 can be checked by means of a simple gauge 16, as shown in FIG. 12a, whose length is adjustable and whose end parts 17 have the same cross-sectional shape as the connecting elements 3. FIG. 12b shows a detail of FIG. 12a on an enlarged scale.

The various embodiments of the bridge framework constructed in accordance with the principles of this invention, and combined with crowns produced by using foil caps, have the following characteristics:

1. The bridge pillars support the crown frameworks;
2. The connecting elements of the bridge frameworks are sunk into cavities prepared in the masticating surfaces, taking the anatomical conditions into consideration;

3. The cavities are produced by means of a standardized cutter;
4. A precise fit can be obtained between the supporting elements and the cavities;
5. The teeth and their roots are subjected exclusively to axial stress;
6. There is negligible tractive force and compressive stress in, and on, the foil cap of the pillar teeth's crown framework;
7. A bridge framework can be developed with a core of high modulus and coating of the outside of pure gold;
8. Automatic fusion occurs between the bridge framework and the foil cap of the pillar teeth's crown framework;
9. Efficient use is obtained through immediate determination of length and separation, by means of marking provided in advance, if necessary; and
10. The framework has well-defined mechanical stability.

If the bridge frameworks of the invention are to be used in combination with the normal production of tooth-replacement crowns, the crown frameworks must first be heated and pressed into the wax impression 19 of the bridge pillars 4 in a warm state. Consequently, a similar adjustment for the later reception of the bridge framework after the bridge pillars' crowns are cast takes place there immediately. After the casting of those pillar crowns, the framework of the invention can be soldered with the pillar crowns in a simple manner.

In that connection, additional prefabricated parts 20 made of a plastic that burns with no residue can be used. These parts can be inserted in the wax impression 19 with the help of the gauge 17, or even a bridge framework whose length has already been adjusted, and they will ensure a precise fit.

Other modifications, revisions, and changes will occur to the skilled artisan in the field of dental technology. However, the appended claims should be broadly construed in a manner consistent with the significant technological advances set forth in this application. Thus, the appended claims should be broadly construed and should not be limited to their literal terms.

We claim:

1. A framework for use in producing tooth-replacement bridges, comprising
   a support bar for spanning a gap that is to be closed between abutment teeth,
   said support bar having opposed ends for positioning the support bar on said teeth,
   at least one longitudinal reinforcing rib extending along the length of said support bar from the bottom thereof to resist bending of said support bar in a vertical plane, and
   at least one lateral rib for resisting bending of said support bar in a horizontal plane.

2. The invention of claim 1, wherein said longitudinal rib has at least one hole extending through its thickness to provide retention means for facing material.

3. The invention of claim 1, comprising a pair of said lateral ribs, wherein the lateral ribs extend horizontally along and from said support bar, on either side thereof.

4. The invention of claim 3 wherein the lateral ribs extend, in a plane perpendicular to the length of the support bar, from the longitudinal rib so as to form therewith a three-dimensional retention-element group for the bridge-facing material.

5. The invention of claim 4, wherein said lateral rib has at least one hole extending through its thickness to provide retention means for facing material.

6. The invention of claim 4, comprising a plurality of said retention element groups corresponding in number to the number of teeth that are to be replaced by a tooth-replacement bridge.

7. The invention of claim 1, wherein the ends of the support bar are provided with a series of markings to facilitate cutting the bar to a desired length.

8. The invention of claim 1 wherein the cross-sectional configuration of the ends of the support bar corresponds to the anatomical contour of the pulp vault and the occlusion field of the abutment teeth.

9. The invention of claim 8 wherein the height of the cross-section of the ends of the support bar is less than the maximum possible preparation depth above the pulp of the abutment teeth.

10. The invention of claim 1 wherein at least one end of the support bar is sufficiently long that it can be set on several abutment teeth simultaneously in order to interlock them with each other.

11. The invention of claim 1, wherein the ends of the support bar are ring-shaped.

12. The invention of claim 1 wherein the framework material is reworked with cold-plastic shaping.

13. The invention of claim 1 wherein the framework is a gold casting.

14. The invention of claim 1 wherein the support bar and longitudinal reinforcing ribs are formed from plural lamina laminated in a direction transverse to the length of the support bar.

15. The invention of claim 14 wherein at least one of said lamina is made of a material with a high modulus of elasticity.

16. The invention of claim 14 wherein the lamina are bonded to each other by cold welding.

17. The invention of claim 1 wherein said reinforcing ribs are fastened to said support bar by colding welding.

* * * * *